(12) United States Patent
Ambrosio et al.

(10) Patent No.: US 8,231,909 B2
(45) Date of Patent: Jul. 31, 2012

(54) INJECTABLE COMPOSITE MATERIAL SUITABLE FOR USE AS A BONE SUBSTITUTE

(75) Inventors: Luigi Ambrosio, Ottaviano (IT); Valeria Sanginario, Pozzuoli (IT); Maria Pau Ginebra, Barcelona (ES); Josep Anton Planell, Barcelona (ES)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 12/979,818

(22) Filed: Dec. 28, 2010

(65) Prior Publication Data

US 2011/0091554 A1    Apr. 21, 2011

Related U.S. Application Data

(63) Continuation of application No. 11/997,211, filed as application No. PCT/IB2006/052623 on Aug. 1, 2006, now abandoned.

(30) Foreign Application Priority Data

Aug. 3, 2005 (IT) .................. TO05A0549

(51) Int. Cl.
*A61K 33/42* (2006.01)
*A61K 8/19* (2006.01)
*A61K 8/24* (2006.01)

(52) U.S. Cl. ........................................ 424/602; 523/105
(58) Field of Classification Search .................. None
See application file for complete search history.

(56) References Cited

FOREIGN PATENT DOCUMENTS

| EP | 1449818 A1 | 8/2004 |
|---|---|---|
| WO | WO 02/070029 A2 | 9/2002 |
| WO | WO2005/025595 * | 3/2005 |
| WO | WO 2005/025595 A2 | 3/2005 |

OTHER PUBLICATIONS

Tas et al., (Key Engineering Materials, 264-268, 2004 pp. 2079-2082, IDS reference).*
Definition of hydrogel on the online Encarta World English Dictionary.*
Bohner, et al., "Injectability of calcium phosphate pastes", Biomaterials, 2005, pp. 1553-1563, vol. 26.
Landi, et al., "Calcium phosphate ceramics as drug-delivery system for anticancer therapy" Key Engineering Materials, 2001, pp. 901-904, vols. 192-195.
Sanginario et al., "Injectable composite hydrogels for orthopaedic applications. Mechanical and morphological analysis" Key Engineering Materials, 2004, pp. 485-488, vols. 254-256.
Tas, "Preparation of porous bioceramics by a simple PVA-processing route" Key Engineering Materials, 2004, pp. 2079-2082, vols. 264-268.
http://encarta.msn.com/encnet/features/dictionary/DictionaryResults.aspx?refid=1861619414.

* cited by examiner

*Primary Examiner* — David J Blanchard
*Assistant Examiner* — Tigabu Kassa
(74) *Attorney, Agent, or Firm* — Rothwell, Figg, Ernst & Manbeck, P.C.

(57) ABSTRACT

The invention relates to a new injectable composite material suitable for use as a bone substitute. The composite material according to the invention comprises a reactive ceramic phase based on tricalcium phosphate and an organic phase comprising a polyvinyl alcohol hydrogel. By varying the concentration of the two phases it is possible to modulate the mechanical and injectability properties of the material.

8 Claims, No Drawings

INJECTABLE COMPOSITE MATERIAL SUITABLE FOR USE AS A BONE SUBSTITUTE

This application is a continuation of U.S. Ser. No. 11/997,211 filed Jan. 29, 2008, now abandoned, which is a 35 U.S.C. §371 National Phase Entry Application from PCT/IB2006/052623, filed Aug. 1, 2006, and designating the United States. This application also claims the benefit of Italian Patent Application No. TO2005A000549 filed Aug. 3, 2005, the disclosure of which is incorporated herein in its entirety by reference.

This invention relates to a new injectable composite material suitable for use as a bone substitute. In particular, the invention relates to an injectable composite material comprising two phases: a ceramic phase and a hydrogel fluid phase.

In orthopaedic surgery, biomaterials can be applied to a number of diseases of the skeletal system where it is necessary to replace or supplement bone tissue, from the most common ones, related to age, such as osteoporosis, bone arthrosis, arthritis, to the most serious ones, such as sarcomas and bone cysts.

In order to provide a bone substitute, it is essential to examine and analyse the natural tissue. Natural bone is a hard tissue of a composite nature, essentially consisting of an organic matrix (collagen fibres) and a ceramic reinforcement (apatite crystals), organised in a complex way to form a highly specialised structure with a targeted anisotropy in its mechanical properties. Bone tissue acts primarily as a supporting and protective framework for internal soft tissues and secondly engages in the exchange of valuable elements such as calcium and magnesium, for which bone constitutes the only reserve present in the body, with the blood and other surrounding fluids.

In order to satisfy this dual function bone tissue undergoes continuous replacement and remodelling. These processes are regulated by a large and complex set of hormonal substances, some of which are produced by bone cells themselves.

The mechanical properties of bone are expressed through its elastic modulus and its maximum compression and tensile strengths. As a general rule, it is known that bone has greater compression strength than tensile strength, and that cortical bone has mechanical properties superior to those of trabecular bone.

The values for elastic modulus reported in the literature vary over a range from 50 MPa to 2 GPa for trabecular bone and from 10 GPa to 22 GPa for cortical bone. Compression strength values are comprised between 1 MPa and 50 MPa for trabecular bone, while for cortical bone they are comprised between 100 MPa and 220 MPa. These values constitute reference values for the mechanical behaviour of bone substitutes. In order to be able to ensure the functional compatibility which is essential for their full incorporation, bone substitutes must in fact have mechanical properties which are as similar as possible to those of the natural bone.

The need for the use of a bone substitute may arise subsequent to fracture of the bone tissue, in cases where the normal processes of repair and re-growth do not take place in physiological time or do not take place at all, or following surgery for the removal of a tumoral mass or bone cyst, in which case there is a need to fill the cavity produced by surgery.

Bone substitute must therefore ensure mechanical stability over clinically acceptable periods and have osteo-compatible properties which encourage the laying down of new tissue. One of the properties which is fundamental for a bone substitute is the possibility of remaining in contact with the natural tissue for an indefinite period of time without the need for surgical removal.

In addition to this, the increasingly wider use of the arthroscopy technique resulted in an increased interest for a search for injectable materials capable of being conveniently inoculated into bone cavities, allowing optimum filling without the need to know their shape and dimensions in advance, or even, when possible, eliminating the need for surgery.

At the present time, the most widely used injectable material in orthopaedic surgery is polymethylmethacrylate (PMMA), which however develops appreciable quantities of heat on application and may result in the necrosis of the tissues with which it comes into contact.

Ceramic materials or cements based on phosphorus and calcium (CPC) have given rise to appreciable interest in applications involving hard mineralised tissues. These materials are in fact non-toxic and non-immunogenic, in that they are essentially composed of calcium and phosphorus ions, which are the natural constituents of the ceramic phase of bone tissue. One of the most useful properties of phosphorus and calcium-based cements (CPC) is the fluid consistency they acquire when they are mixed with an aqueous liquid phase on preparation. A further useful property of these cements is their ability to harden in the presence of the water used for preparation.

Among the CPC, tricalcium phosphate (TCP) is capable of binding directly to bone tissue, thus forming a very strong interface bond between the material and the tissue.

Tricalcium phosphate, like all calcium phosphate-based bone cements (CPBC), is a naturally porous material, but its mechanical behaviour is typical of a brittle material, which is therefore very different from the behaviour of natural bone tissue.

Furthermore, as it is often found in the literature, the paste which is obtained during the preparation of TCP risks disintegration in contact with biological fluids if applied prematurely, while if applied too late it hardens and becomes rather unmanageable. Finally, when the paste is extruded through a syringe it frequently occurs that the two phases separate, and as a consequence most of the liquid phase escapes while the solids remain trapped in the syringe.

Patent application WO 02/070029 describes a workable mixture which is suitable for use as a bone substitute, comprising porous β-TCP and a binder selected from conventional emulsifying, suspension, thickening, gelling, binding, disintegrating or stabilising agents. Among the binding agents, sodium alginate, hyaluronic acid, cellulose and cellulose derivatives, collagen, peptides, mucin, chondroitin sulphate and the like, are specifically mentioned.

Hydrogels are materials known per se, which have been the subject-matter of particular interest in medical and scientific research during the last decade, in particular in the field of biomedical applications. Their typical network structure, that is to say a structure of chemically or physically cross-linked polymer chains, in fact makes them capable of absorbing and retaining a substantial quantity of liquid, water or biological fluids without dissolving. Specifically, their appreciable water content has the result that the interfacial tension which arises in contact with biological fluids is very low. This important property, associated with the permeability of hydrogels in comparison with small molecules such as metabolites or nutrients, renders them particularly similar to biological tissues. Disadvantageously, however, they have poor mechanical properties, which greatly reduce their possibility of application as such as materials for artificial implants.

The inventors have found that the combination of a polyvinyl alcohol hydrogel and a tricalcium phosphate (TCP) ceramic phase makes it possible to obtain a composite material having optimum mechanical properties which are surprisingly similar to those of natural bone. The composite material obtained is also characterized by improved injectability compared to that of TCP alone.

The inventors have also found that by varying the concentration of the two phases it is possible to modulate the mechanical and injectability properties of the composite material obtained, based on the specific requirements of the case.

One aspect of the present invention is therefore an injectable composite material which is particularly suitable for use as a bone substitute, comprising a tricalcium phosphate ceramic phase and a polyvinyl alcohol hydrogel fluid phase.

The composite material according to the invention advantageously has mechanical properties which are very similar to those of the natural tissue. It is also characterized by improved injectability and consequently greater ease of application in comparison with conventional tricalcium phosphate-based cements.

The injectable composite material of the invention is prepared as follows.

An aqueous solution of polyvinyl alcohol (PVA) is prepared in a predetermined concentration, preferably within the range from 2% to 30% by weight, even more preferably between 10% and 20% by weight. Subsequently, the aqueous PVA solution is mixed with tricalcium phosphate powder, preferably α-tricalcium phosphate, so as to obtain a pasty material capable of being injected into bone cavities, where it can harden as a result of both the water present in the material and the water present in the surrounding environment.

Preferably, the injectable composite material according to the invention has a polyvinyl alcohol polymer/tricalcium phosphate ratio by weight lying within the range 3/97 to 20/80 (w/w).

Mechanical Properties

Aqueous solutions were prepared with different concentrations by weight of PVA (10%, 17%, 20%) in order to investigate the mechanical and injectability properties of the composite material according to the invention. These solutions were prepared by mixing the polymer powder with water at a temperature of 100° C. for 20 minutes. After cooling to ambient temperature, the polymer solutions were mixed with α-TCP powder in order to obtain three different compositions of α-TCP/PVA by weight (93/7, 88/12, 86/14 w/w).

In order to examine its mechanical properties, the pasty composite material so obtained was injected into Teflon discs having an appropriate geometry and immersed for 4 days in an aqueous solution of $NaH_2PO_4$ (2.5% by weight) at 37° C. to promote hardening.

The compression test results (ASTM D695) shown in Table 1 demonstrate that it is possible to modulate the mechanical behaviour of the composite material (α-TCP/PVA) by using different percentages by weight of the polymer and inorganic phase. In particular, specific compositions of these composites exhibit mechanical properties which are even better than those of calcium phosphate alone. In fact, using a percentage of polymer phase up to 7% by weight, a composite (93/7) is obtained, having a maximum compression strength $\sigma_{max}$ increased from the value of 21±3 MPa, recorded for α-TCP alone, to the value of 25±5 MPa. Similarly, the elastic modulus E increases from a value of 0.8 GPa to a value of 1.2 GPa. A slight increase in the maximum deformation $\epsilon_{max}$, i.e., the value of the deformation recorded at the maximum compression strength, is also found (0.02±0.01 mm/mm for α-TCP alone, 0.03±0.01 mm/mm for the composite according to the invention), while an appreciable increase in the ultimate deformation εu, i.e., the deformation recorded at the breaking point of the material, is obtained, increasing from 0.06±0.01 mm/mm for α-TCP alone to 0.09±0.01 mm/mm for the composite according to the invention. From the practical point of view, this results in a greater deformability of the composite material prior to breaking compared to cement. This may also be expressed in terms of toughness, which can be calculated as the area subtended by the mechanical curve, which triples in value (2.1 MPa) in the case of the composite in comparison with α-TCP alone (0.7 MPa).

From Table 1 it also clearly appears that with percentages over 7% by weight, composite materials are obtained having a compression strength and an elastic modulus lower than or equal to those of the starting cement alone (α-TCP). The $\sigma_{max}$ value, in fact, decreases to 17±1 MPa for the α-TCP/PVA 88/12 composite and even to 14±3 MPa for the α-TCP/PVA 86/14 composite, whilst the elastic modulus values remain almost unchanged. However, the maximum deformation $\epsilon_{max}$ increases up to values of 0.04±0.01 mm/mm for the 88/12 composite and 0.05±0.01 mm/mm for the 86/14 composite. As far as ultimate deformation εu is concerned, the 88/12 composite has a value of 0.08±0.01 mm/mm, which is slightly different from the 93/7 composite, whilst the value for the 86/14 composite appreciably increases up to a value of 0.11±0.01 mm/mm. Specifically, as a result of the increase in the two deformation values, the toughness values recorded for both the 88/12 composite (T=1.1 MPa) and the 86/14 composite (T=1.0 MPa) are greater than those for the cement alone (α-TCP).

From a comparison between the values obtained from the mechanical tests and the ones previously reported in connection with natural bone tissue, it results that the mechanical properties of the injectable bone substitute according to the invention lie within the range of values of trabecular bone tissue.

Injectability

In order to evaluate the range of applicability of the composite material according to the invention and to compare it with the conventional cements based on calcium phosphate, the experimental parameter of injectability was used, this being defined as the percentage by weight of the material which can be extruded from a syringe.

Injectability can be expressed by the following relationship:

$$\% I = \frac{W_e}{W_i}$$

In order to determine injectability, syringes filled with a known quantity of material ($W_1$) were used, and they were subjected to a compressive force by means of a dynamometric machine in which the rate of descent of the crossbrace was 15 mm/min and the applied load was approximately 100 N. Once the components had been weighed, they were mixed until a pasty consistency was achieved for the composite, which was then placed in the syringe, which was in turn mounted on a suitable support. These operations had to be carried out in 60-90 seconds. After the syringe was filled, the time count for the test could begin. When the test was complete, the extruded material was weighed ($W_e$) and the desired parameter was calculated.

Table 2 shows that, in connection with the practical application of the material, the addition of a PVA hydrogel produces various benefits. The first substantial positive effect is that the paste obtained has an optimum consistency for extrusion through a syringe and no further phenomena of separation between the two phases occur, as sometimes happens when α-TCP is used alone. The second important positive aspect is the appreciable length of time at the medical practitioner's disposal (1 hour) for applying the composite material before it hardens. The increase is significant (see Table 2) when compared with α-TCP alone, for which 91% of the loaded amount remains trapped and can no longer be injected after only 6 minutes.

From a more general point of view, the advantage of associating a PVA hydrogel with tricalcium phosphate lies in the fact that the water retained in the hydrogel is slowly and completely released to the ceramic phase, providing for a uniform crystal precipitation and consequently final hardening of the composite even in the absence of an external aqueous solution. It has also been observed that no appreciable increase in the temperature occurs during hardening of the injectable composite material.

The injectable composite material according to the invention may also contain a bioactive agent (i.e., a substance having biological activity) selected for example from drugs, cells, growth factors and the like, possibly in a form suitable for a controlled kinetics-release during application.

TABLE 1

Mechanical properties under compression

| Material | E (GPa) | σmax (Mpa) | εmax (mm/mm) | εu (mm/mm) | T (MPa) |
|---|---|---|---|---|---|
| 100% α-TCP | 0.8 ± 0.2 | 21 ± 3 | 0.02 ± 0.01 | 0.06 ± 0.01 | 0.7 |
| PVA + 93% α-TCP | 1.2 ± 0.1 | 25 ± 5 | 0.03 ± 0.01 | 0.09 ± 0.01 | 2.1 |
| PVA + 88% α-TCP | 0.7 ± 0.3 | 17 ± 1 | 0.04 ± 0.01 | 0.08 ± 0.02 | 1.1 |
| PVA + 86% α-TCP | 0.9 ± 0.1 | 14 ± 3 | 0.05 ± 0.01 | 0.11 ± 0.02 | 1.0 |

TABLE 2

Injectability properties

| Solid phase | Liquid phase | Waiting time (min) | % I |
|---|---|---|---|
| α-TCP | Water + 2.5% wt $NaH_2PO_4$ | 2 | 44.2% |
| α-TCP | Water + 2.5% wt $NaH_2PO_4$ | 3 | 30.9% |
| α-TCP | Water + 2.5% wt $NaH_2PO_4$ | 5 | 18.8% |
| α-TCP | Water + 2.5% wt $NaH_2PO_4$ | 6 | 9% |
| α-TCP | 10% wt PVA Sol | 7 | 100% |
| α-TCP | 10% wt PVA Sol | 20 | 100% |
| α-TCP | 10% wt PVA Sol | 40 | 100% |
| α-TCP | 10% wt PVA Sol | 60 | 95.6% |

The invention claimed is:

1. A method for replacing or supplementing bone tissue comprising administering an injectable composite material consisting of a tricalcium phosphate ceramic phase and a polyvinyl alcohol hydrogel fluid phase to a patient in need of such treatment.

2. The method according to claim 1, wherein the polyvinyl alcohol hydrogel fluid phase is an aqueous solution of 2-30% by weight of polyvinyl alcohol.

3. The method according to claim 1, having a polyvinyl alcohol polymer/tricalcium phosphate ratio by weight within the range of 3/97 to 20/80 (w/w).

4. The method according to claim 3, having a polyvinyl alcohol polymer/tricalcium phosphate ratio by weight of 7/93 (w/w).

5. The method according to claim 3, having a polyvinyl alcohol polymer/tricalcium phosphate ratio by weight of 12/88 (w/w).

6. The method according to claim 3, having a polyvinyl alcohol polymer/tricalcium phosphate ratio by weight of 14/86 (w/w).

7. The method according to claim 1, further comprising administering a bioactive agent selected from a drug, a cell culture, or combinations thereof.

8. The method according to claim 1, wherein the injectable composite material acts as a bone substitute.

\* \* \* \* \*